United States Patent [19]

Kinney et al.

[11] 4,001,460
[45] Jan. 4, 1977

[54] LIGHT MICROSCOPY PROCESSING METHOD

[76] Inventors: Thomas D. Kinney, 3120 Devon Road, Durham, N.C. 27707; John E. P. Pickett, 3323 Pinafore Drive, Durham, N.C. 22705

[22] Filed: Mar. 5, 1975

[21] Appl. No.: 555,392

Related U.S. Application Data

[62] Division of Ser. No. 463,055, April 22, 1974, Pat. No. 3,892,197.

[52] U.S. Cl. .................................. 427/2; 427/299
[51] Int. Cl.² .......................................... A01N 1/02
[58] Field of Search ............... 427/2, 299; 424/3; 118/4, 7, 11, 50; 134/94, 95, 96

[56] References Cited

UNITED STATES PATENTS

| | | | |
|---|---|---|---|
| 2,684,925 | 7/1954 | Ferrari | 424/3 |
| 2,899,363 | 8/1959 | Nieburgs | 424/3 |
| 2,959,151 | 11/1960 | Ehrlich | 134/94 |
| 3,227,130 | 1/1966 | Weiskopf | 134/95 |
| 3,400,726 | 9/1968 | DuGrail | 134/95 |
| 3,771,490 | 11/1973 | Kinney et al. | 118/7 |
| 3,807,353 | 4/1974 | Kobernick | 118/11 |
| 3,854,440 | 12/1974 | Astle | 118/7 |
| 3,889,014 | 6/1975 | Kinney et al. | 427/4 |

*Primary Examiner*—Michael R. Lusignan
*Assistant Examiner*—Dennis C. Konopacki
*Attorney, Agent, or Firm*—B. B. Olive

[57] ABSTRACT

A tissue processing method utilizes a closed system for sequentially immersing light microscopy tissue specimens in treating fluids preparatory to embedding or in staining fluids. Treating or staining fluids, including paraffin, are drawn into the processing chamber by use of vacuum and are forced back to their respective containers by use of pressure and the specimens remain substantially stationary throughout the fluid treatment.

7 Claims, 9 Drawing Figures

LIGHT MICROSCOPY PROCESSING METHOD

RELATED COPENDING APPLICATIONS

This application is a division of copending application Ser. No. 463,055, entitled "Light Microscopy Processing Apparatus", filed Apr. 22, 1974, now U.S. Pat. No. 3,892,197.

BACKGROUND OF THE INVENTION

1. Field of the Invention

This invention relates to tissue processing methods and more specifically to a method of processing tissue for light microscopy examination.

2. Description of the Prior Art

The processing of tissue for both electron and light microscopy examination has been the subject of step-by-step improvement. Automatic processing of tissue for electron microscopy tissue processing has been achieved as exemplified in applicant's U.S. Pat Nos. 3,526,203 and 3,771,490.

Automated processing of tissue for light microscopy examination has been achieved as exemplified in the method used in the so-called "Technicon" tissue processor; however, there has been no successful method which would allow light microscopy tissues to be processed in a completely automatic sequence, while being held in an entirely closed system and without requiring substantial movement of the specimens. The availability of a method of processing in a closed system is of critical importance in view of recently published Federal regulations governing handling of hazardous vapors and fumes.

Representative prior art includes U.S. Pat. Nos. 3,227,130; 2,959,151; 2,386,079; 2,341,198; 2,157,875; 2,959,151; 3,400,726; 2,681,298; and 2,684,925.

A review of the prior art further reveals that treating fluids in light microscopy processors are normally required to be recirculated. The processing fluids may be manually returned to their respective containers after use. Processing takes place in open or loosely covered chambers which are not suitable for holding pressure or vacuum conditions. Many of the prior art light microscopy processors, e.g., the so-called "Technicon" tissue processor, also depend upon substantial movement and dipping motions of the tissue specimens into open containers. Any motion of the specimens during processing, of course, tends to damage the specimens of carried to excess.

The prior art has also dealt with the problem of heating paraffin fluids in containers, flow lines, valves, and the like. However, no prior art light microscopy processor, so far as is known, has handled this problem successfully by processing the tissue in a closed, effectively sealed system and in a manner enabling the paraffin fluid to be reused. A fluid flow stainer useful only for staining has been marketed by Lipshaw Manufacturing Company of Detroit, Michigan. This apparatus recirculates staining fluids with a pressure-vacuum system applied to the staining fluid containers but it is not useful for processing tissue, does not provide a pressure vessel type chamber, and cannot handle paraffin.

In summary, the prior art in its present state does not embody a practical, reliable and automatic method of processing useful primarily for processing, including use of melted paraffin, but adapted to staining light microscopy tissue specimens with a minimum amount of handling of the tissue specimens, with maximum economy of the treating fluids, and in a closed system which substantially eliminates dangers from hazardous treating fluid fumes.

SUMMARY OF THE INVENTION

The method of the invention utilizes a plurality of containers of treating fluids, including paraffin, which are drawn to a sealed processing chamber by vacuum and returned by pressure which is applied to the chamber. The tissue specimens are confined in the processing chamber under sealed cover and remain stationary during processing. Fixation, processing, and clearing solutions are directed to the processing chamber in programmed sequence. The paraffin containers are arranged in immediate proximity to the processing chamber which substantially reduces the heating problem and the paraffin in the second, less contaminated, paraffin container can, at any time, be pumped to the first container, the first container paraffin pumped to waste and the second container paraffin replaced in order to minimize paraffin consumption. The method may be practiced in an apparatus unified in a table mounted cabinet.

DETAILED DESCRIPTION OF THE PREFERRED EMBODIMENT

Figure 5:
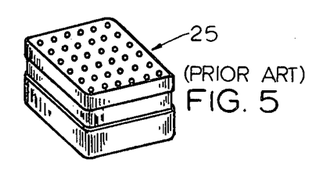
FIG. 5 is a perspective view of a tissue processing and embedding receptacle used in the method of the invention.

In reference to the drawings, a suitable perforated tissue receptacle 25 for holding the tissue specimens to be processed is generally shown in FIG. 5 and is known in the art as a "TIMS" tissue receptacle. For a more detailed description of TIMS tissue receptacles used in paraffin embedding histological tissue sections, reference is made to U.S. Pat. No. 3,411,185 issued on Nov. 19, 1968 and entitled "Composite Histologic Tissue Receptacle". A typical receptacle has a removable cover and may contain one or more tissue samples in the receptacle body cavity to be fixed, dehydrated, cleared, and paraffin embedded prior to being thin sectioned on a rotary microtome. Fluids pass through perforations in the receptacle which is made of materials inert to the fluids.

As previously mentioned, the light microscopy tissue processing method of the invention is directed to a closed system which allows a plurality of perforated tissue receptacles 25 to be processed simultaneously in a sealed chamber according to a scheduled time sequence, through various selected processing solutions among which are fixatives, dehydrants, clearing solutions and liquid paraffin. The particular solutions used and the particular time sequence for each may vary according to different programs. Also, staining solutions may be programmed for exchange between the chamber and the containers when holding staining fluids.

Figure 1:
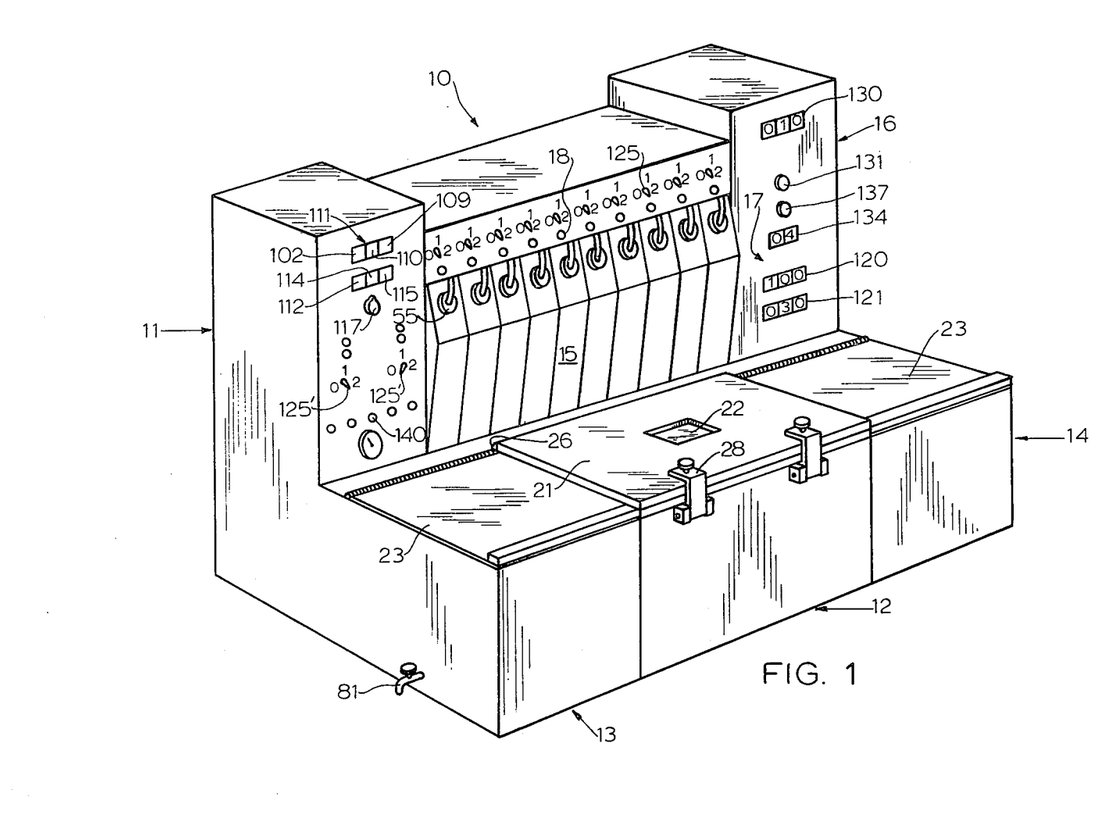
FIG. 1 is a perspective view of a processing apparatus suited to the invention method and embodied in a cabinet for table top support.

Referring now to FIG. 1, an automatic light microscopy tissue processor 10 useful with a preferred method includes a cabinet adapted for table top support; a pair of laterally spaced, upper rearward control compartments 11, 16; a lower, centrally and forwardly located tissue processing chamber 12; a pair of lower, laterally and forwardly spaced heated liquid paraffin containers 13, 14; a plurality of solution containers 15 in an upper central rearward compartment for holding the selectively communicated fluids for processing chamber 12; timing controls 17; and appropriate container signal lights 18.

Figure 6:
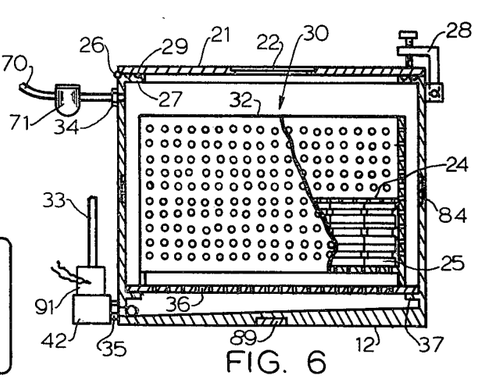
FIG. 6 is a side cross-sectional view of the processing chamber showing a processing receptacle basket in partial cutaway view revealing installed tissue processing receptacles.

Processing chamber 12 remains stationary and includes a tiltable lid 21 having a window 22. Lid 21 has a hinge 26 and is secured to processing chamber 12 in a substantially air tight, sealed relation by appropriate latches 28 and a rim 27 and gaskets 29 (indicated in FIG. 6). Processing chamber 12 is adapted to receive a plurality of tissue processing receptacles 25, best shown in FIG. 5, and more fully described in the mentioned U.S. Pat. No. 3,411,185. As best illustrated in FIG. 6, a basket structure 30 having perforated sidewalls 32 receives said receptacles and supports a plurality of such tissue receptacles 25 within processing chamber 12. Also shown in FIG. 6, is an appropriate pressure and vacuum inlet coupling 34 as well as fluid line coupling 35 which communicate with the interior of said processing chamber 12. A suitable rectangular perforate plate 24 provides weight sufficient to overcome the buoyancy of the tissue receptacles 25 and keeps them submerged during processing.

Figure 2:
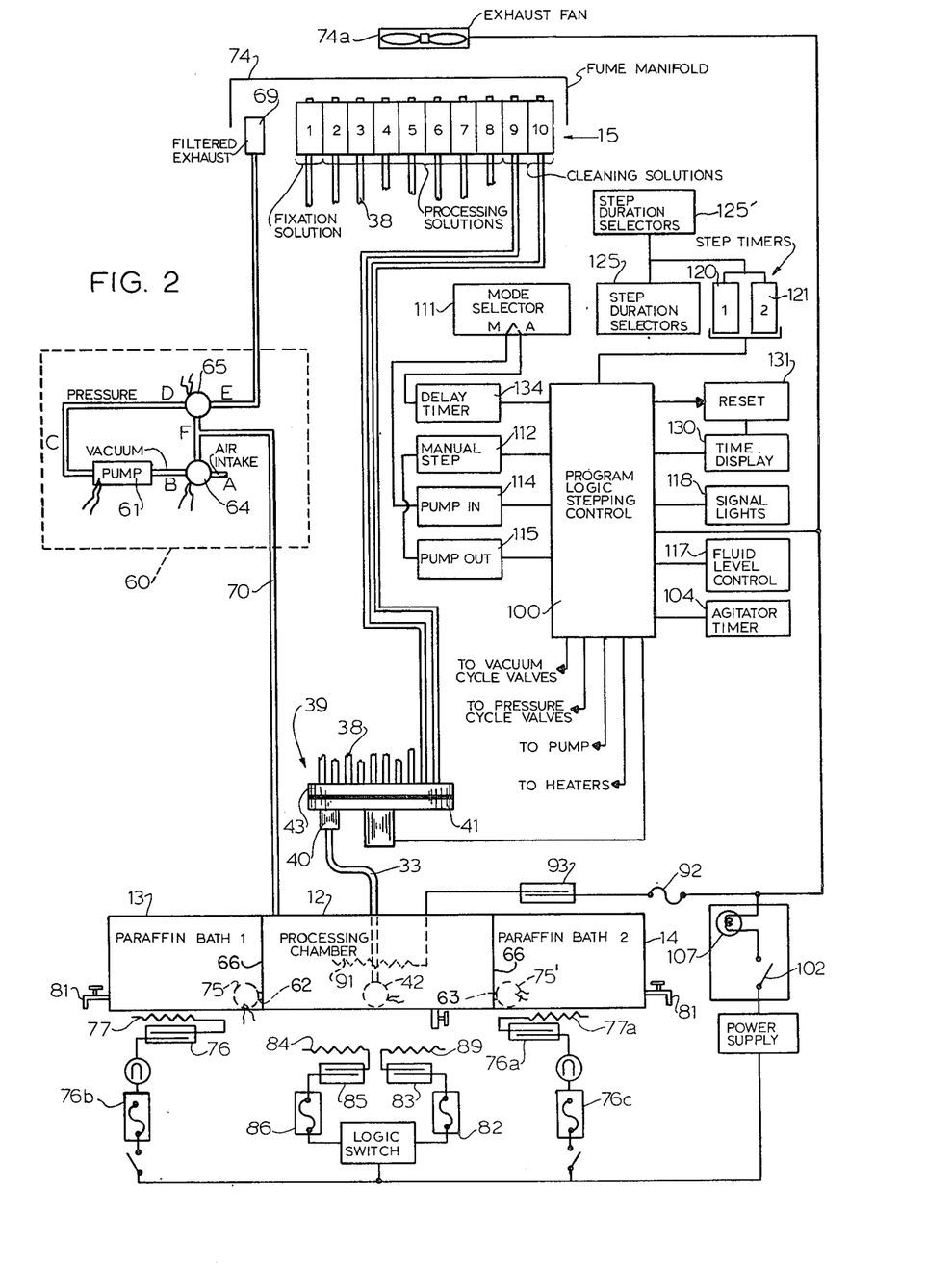
FIG. 2 is a somewhat schematic diagram of the apparatus showing particularly a preferred fluid flow configuration based on use of vacuum and pressure applied to a sealed processing chamber.

Referring now to FIG. 2, solution containers 15 are connected to processing chamber 12 by individual conduits 38 which communicate with a rotary valve structure 39 and then through a common conduit 33 to electrically operated valve 42 and from there directly into processing chamber 12. When solutions are returned to their containers, they simply retrace the supply route in reverse. Rotary valves as such are known and while a single rotary valve as illustrated has many advantages, a solenoid valve at each container could be employed to achieve selection and controlled fluid flow in conjunction with the unique paraffin related apparatus later described.

Water base solutions, such as Zenker's, formalin and water, are effectively kept separated from oil base solutions such as xylene, the combination of which causes formation of an emulsion. Typically, then, for the ten numbered solutions shown, the invention contemplates that solution one will be fixative, e.g., Zenker's or formalin; solutions two through six will comprise various percentages of alcohol for dehydrating; and solutions seven and eight are xylene for clearing. Further solutions such as xylene and alcohol will be contained in containers nine and ten for purposes of cleaning processing chamber 12 following a completed processing sequence and withdrawal of processed tissue specimens from chamber 12.

The following table shows a series of processing and cleaning solutions which might typically be used according to the invention:

|  | Container No. | Solution |
| --- | --- | --- |
| Processing Cycle | 1 | Zenker's (or formalin) |
|  | 2 | 70% Alcohol |
|  | 3 | 80% Alcohol |
|  | 4 | 95% Alcohol |
|  | 5 | Absolute Alcohol |
|  | 6 | Absolute Alcohol |
|  | 7 | Xylene |
|  | 8 | Xylene |
|  | Paraffin I |  |
|  | Paraffin II |  |
| Cleaning Cycle | 9 | Xylene |
|  | 10 | Absolute Alcohol |
|  | Additional water rinses manually done, if desired. |  |

Figure 3:
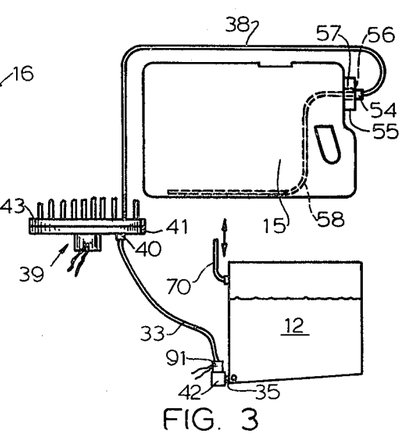
FIG. 3 is a partial side view showing the processing chamber coupled to one of the processing solution containers through a rotary valve mechanism by appropriate fluid lines, other containers being similarly coupled.
Figure 4:
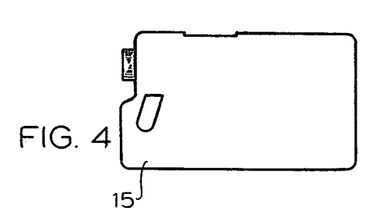
FIG. 4 is a side view to illustrate the shape of a processing solution container found useful for the substantially sealed, fumeless method of the invention.

Referring now to FIG. 3, a typical processing solution container 15 of a commercially available shape as in FIG. 4, conduit 38, rotary valve 39 made up of rotatable plate 41 and fixed plate 43, common conduit 33, valve 42 and processing chamber 12 are shown in operative assembly. A suitable swivel connection 40 allows the movable rotary valve plate 41 of rotary valve 39 to rotate. While FIG. 3 only illustrates the fluid path for only one solution container 15, it should be clear from FIG. 2 that there are in fact ten solution containers, all of which feed into rotary valve 39 and then into common conduit 33. Container 15 of FIG. 3 is shown having a fitting 54 which will facilitate rapid changing of solution containers. A tube 58 communicates with the bottom of container 15 to drain the entire contents, if desired, during processing.

As previously mentioned, the processor is operated so that all solution admission, solution retention and solution drainage takes place in automatic or alternately, manual timed sequence and in a substantially closed system. Selective application of air pressure and partial vacuum to the sealed processing chamber 12 in conjunction with operation of valve 42, etc., enables rapid transfer of processing solutions from containers 15 to chamber 12 and back to containers 15 again.

With specific reference again to FIG. 2, a combined vacuum and pressure system 60 is shown in dashed lines and comprises a pressure pump 61 having means for providing pressure as well as partial vacuum as indicated and remotely operable valve means 64, 65, for selecting whether vacuum or pressure is applied to an air line 70 communicating with processing chamber 12.

Referring again to FIG. 3, solution admission and drainage from chamber 12 and fluid measurement is controlled by selective application of pressure and partial vacuum to the chamber 12 via the air line 70 in conjunction with timed operation of the remotely operable rotary valve 39 and remotely operable valve 42. Air line 70 preferably connects to the interior of line 20 at a relatively high location near the cover as illustrated which avoids entry of the solutions into chamber 12. By creating a timed partial vacuum in chamber 12, a selected fluid is drawn into the chamber, and by pressurizing chamber 12 the fluid is expelled from the chamber. Reference will next be made to FIG. 2 for a discussion of one pressure, vacuum and rotary valve arrangement useful in the invention, and then to FIGS. 2 and 7 for a description of liquid paraffin flow to and from chamber 12 according to the invention. Since rotary valves are known, no detailed description of valve 39 is deemed necessary.

Referring again to FIG. 2, in a "pump in" cycle fluid flow to processing chamber 12 from any given solution container 15 or paraffin containers 13 or 14 is effected by creating a timed, partial vacuum in the sealed processing chamber 12. In the diagram shown, this is accomplished by actuating valve 64 to enable air to flow between F and B, by energizing pump 61, and by actuating valve 65 to enable air to flow between D and E on a timed schedule. Simultaneous with the application of a partial vacuum to chamber 12, rotary valve 39 rotates to provide a path through valve 39 for the desired solution to flow through valve 39, into conduit 33, through valve 42 and on into processing chamber 12. As an example, to move a measured quantity of solution number one to chamber 12, rotary valve 39 is energized and plate 41 is rotated until the line 38 from container number one lines up with the conduit 33 opening and valve 42 is opened on a timed schedule. Air drawn from chamber 12 during such vacuum cycle is expelled to atmosphere by means of a filtered exhaust 69 which is located so as to have its fumes withdrawn as illustrated in FIG. 2. Alternatively, in a "pump out" cycle to effect fluid flow back to a selected solution container 15, chamber 12 is pressurized above atmosphere by actuating valve 64 to permit air to flow between A and B, and by actuating valve 65 to permit air to flow between D and F. Air is taken into pump 61 by means of an intake opening at A. Suitably, valve 42 and rotary valve 39 assume the same open position as on the vacuum or "pump in" cycle to enable fluid to flow back into the appropriate container 15. The fluid and air line valves normally remain closed while a "pump in" or "pump out" cycle is not in progress with the exception of the air line valves used during vacuum and pressurized agitation later described. Valve 42 is located immediately adjacent the rear wall and is closely coupled to chamber 12 and is positioned proximate the bottom wall of chamber 12. This position facilitates entry and drainage of fluids. Also, by keeping valve 42 closed during use of paraffin, there is minimum opportunity for the paraffin to block valve 42.

Referring again to FIG. 3, the previously referred to solution containers 15 (with operating numbers 1 through 10) have respective caps 55 for refilling the containers. Suitable air vents 56, indicated by dashed lines, are provided in each cap 55, but are preferably kept extremely small so as to limit any admission of moisture. Caps 55 may also be provided with dessicant material 57 to keep certain solutions, e.g., absolute alcohol substantially free from moisture. As illustrated in FIGS. 1 and 2, fluid vapors vented to atmosphere during normal operation of processor 10 are collected by a fume manifold 74 serving as a top portion of housing 11 and are exhausted by an appropriate fan 74a. A suitable trap in line 70 filters fumes, et cetera.

Figure 7:
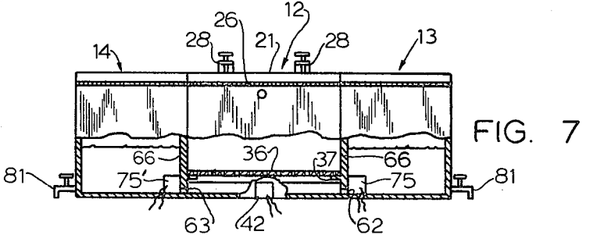
FIG. 7 is a rear cutaway view of the processing chamber and liquid paraffin containers.

Referring next to FIG. 7, liquid paraffin is stored in two heated and temperature controlled, laterally spaced containers 13 and 14 residing immediately adjacent and on either side of processing chamber 12. Transport of liquid paraffin from either container 13 or 14 to chamber 12 is preferably accomplished by use of valves 75, 75' which are illustrated in submersed positions immediately adjacent and near the bottom wall of chamber 12. Respective conduit means 62, 63 communicate valves 75, 75' with chamber 12 as shown. This arrangement enables the heating elements 77, 77a (shown schematically in FIG. 2) which are integral with paraffin container 13, 14 respectively to maintain the correct temperature in the liquid paraffin as well as in the respective valves 75, 75' and the conduits 62, 63. Thermostats 76 76a and thermal fuses 76b, 76c maintain the desired temperature and prevent overheating. Valves 75, 75' may also be located externally of the respective paraffin containers but should have close, i.e., minimal distance couplings both to the paraffin containers 13, 14 and to chamber 12 and should be near their bottom walls.

It should be noted that the provision for two separate paraffin stages as embodied by the invention enables substantially complete paraffin impregnation of tissue specimens prior to paraffin embedding. While one paraffin stage could be used, use of two paraffin stages is generally consistent with current tissue processing technique, although variation on the exact number of paraffin steps may occur between different histological technicians. Paraffin containers 13 and 14 may be formed substantially integral with processing chamber 12 separated only by common partitions 66. A lid 23 on each paraffin container 13 and 14 is hinged and may be periodically opened to replenish the supply of paraffin, while respective manual drain means 81 may be used to drain the used, impure paraffin. Paraffin containers 13 and 14 are not required to be pressure sealed but should preferably be closed to atmosphere contamination.

As will be described later, control means are provided in the apparatus enabling transport of a body of liquid paraffin from one paraffin container to the opposite paraffin container enabling impure paraffin used, say, in the next sequential step following the last step of xylene (solution 8 of FIG. 2) to be periodically drained and replaced with less impure paraffin previously used in the final processing step. This enables a substantially pure body of paraffin to be maintained for the last processing step, but makes use, through an automatic "paraffin exchange" step, of slightly impure paraffin for the next to the last processing step. Such exchange of paraffin is contemplated every sixth processing sequence.

Prior to discussing the programming sequence reference is again made to schematic diagram of FIG. 2 wherein note should be taken of the use of a dual heating element to heat processing chamber 12. A first heating element 84, located in the side wall of processing chamber 12 (see FIG. 6), is adapted to gradually provide heat to said chamber 12 from the first processing step until the first paraffin step (after sequential solution 8 of FIG. 2) and is set by thermostat 85 and by thermal fuse 86 to approach but not to exceed 42° C. Slight heating of chamber 12 throughout the early tissue processing sequence, e.g., fixative, dehydrating, and clearing steps enables better solution penetration into the tissue and also provides a pre-heated container prior to entry of melted paraffin. Temperature must be restricted during the steps of such volatile solutions as alcohol and xylene. Once the first paraffin step is reached, however, second heating element 89, located in the base of processing chamber 12 (see FIG. 6) is adapted to be energized raising the temperature within chamber 12 to 62° C. It should be noted that the lag time for this necessary temperature rise need only be very short, e.g., 15 seconds, since chamber 12 approximates 62° C immediately prior to the first paraffin step. Thermal fuse 82 and thermostat 83 prevent overheating of chamber 12 during paraffin steps. While heaters 84 and 89 are shown in a preferred location, alternate locations might be chosen to achieve the desired result of even temperature throughout processing chamber 12. As seen in FIGS. 3 and 6, a third heating element 91 is located adjacent the rear wall of chamber 12. Element 91 effectively maintains a suitable operating temperature on valve 42 and minimizes clogging by any paraffin which happens to enter the valve port adjacent chamber 12. Thermal fuse 92 and thermostat 93 prevent overheating of chamber 12. The overall heating is also designed to maintain all paraffin carrying pipes at an above melting temperature.

As heretofore described, vacuum and pressure conditions are selectively applied to the sealed processing chamber 12 and are effectively used to transport the various processing and cleaning solutions to and from the processing chamber. An advantageous feature of this arrangement resides in the capacity to use remotely and electrically operated valves, heaters and the electrically operated air pump 61. Another advantage is the capacity to apply such vacuum or alternating vacuum and pressure to the processing chamber while a selected solution is in the chamber, to enhance solution penetration into the tissue being processed. In addition, vacuum or alternating vacuum and pressure applied to solutions in chamber 12 may result in improved penetration of tissue in the receptacles installed in the chamber due to trapped air bubbles being freed.

Referring again to FIG. 2, vacuum or alternating vacuum and pressure applied to chamber 12 during processing of given solutions (including paraffin) hereinafter referred to as an "agitation cycle" is preferably conducted at periodic intervals, e.g., every 10 minutes while each of selected processing solutions is in chamber 12. The term "agitation" is used in a loose sense to mean increasing tissue penetration by vacuum or pressure, releasing air bubbles, and the like. It has previously been mentioned that air valves 64 and 65 and fluid valves 42 and 39 remain closed while a given solution is not being pumped to or from chamber 12.

To create a partial vacuum in chamber 12 for purposes of "agitation" valves 64 and 65 are set to the previously described "vacuum cycle" positions, and pump 61 is energized for a predetermined period of time set by an "agitator" timer 104 (not shown on control panel). A vacuum of −22 p.s.i. may be exerted for example. The invention also contemplates the use of a partial vacuum periodically during given solution steps and a pressure during other solution steps. Pressure may be applied by moving valves 64 and 65 to the respective "pressure cycle" positions and energizing the electrically operated air pump 61. It is apparent that suitable programming of alternating pressure and vacuum agitation cycles or simply of intermittent vacuum cycles may be readily accomplished by stepping switches or logic circuitry well known to those skilled in the art.

The program logic and stepping control 100 employed by the present apparatus may comprise a suitable rotary stepping switch having a clock drive, or preferably solid state logic circuitry. In any case, the logic or stepping mechanism involved is deemed well within the related art so as to not require detailed elaboration herein. The general type of circuitry required has been illustrated in FIG. 2 and is of the type generally described, for example, in prior U.S. Pat. No. 3,771,490. In order to illustrate typical operations of the described processing apparatus, however, the description will now briefly describe a series of controls and their preferred functions.

Figure 8:
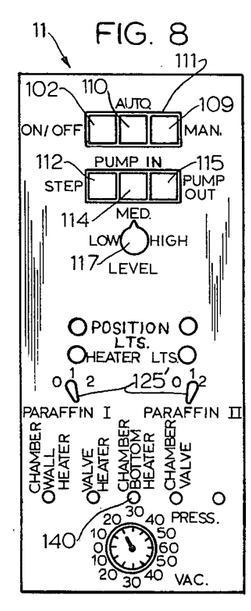
FIG. 8 is a front view of the left side control panel of the apparatus used in practicing the invention.
Figure 9:
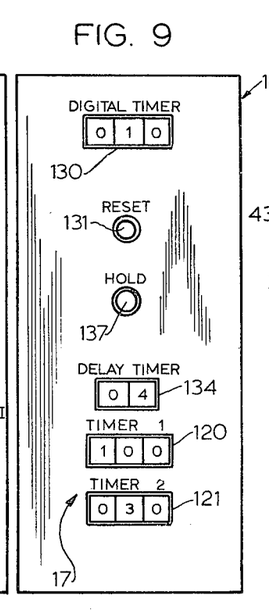
FIG. 9 is a front view of the right side control panel of the apparatus used in practicing the invention.

Referring now to FIGS. 2, 8 and 9, an on-off switch 102 controls power to the processor program and stepping control 100. The power is preferably continuously supplied to paraffin bath heating elements 77 and 77a via thermostats 76, 76a and thermal fuses 76b, 76c to maintain the paraffin contained in baths 13, 14 above melting point even while processor 10 is idle. Thus, the paraffin temperature is preferably unaffected by operation of on-off switch 102. Switch 102 preferably contains a suitable indicator lamp 107 to indicated to the operator that the processor is energized. Selective manual or automatic operation is provided by a mode selector switch 111. For manual operation switch 109 is employed and for automatic operation switch 110 is employed. Manual control of sequential, i.e., step-by-step, processing steps is provided by push button switch 112 and which causes illumination of solution signal lights 18 (see also FIG. 1). Manual solution pumping in or pumping out cycles are controlled by switches 114 and 115, respectively, which govern vacuum and pressure cycles of the vacuum pressure system 60. The signal lights 18 are preferably arranged to illuminate to half intensity indicating which step the processor has reached, and to full intensity whenever the respective solution is being pumped to or from chamber 12. A level control switch 117 provides a choice between high, medium, and low solution levels in chamber 12 by controlling the length of time which pump 61 operates during a given solution pump-in or pump-out. Thus, processor 10 is adapted to handle either relatively large or small quantities of processing receptacles.

For determining the length of time the tissue samples are exposed to each processing solution, a pair of manually set timers 120, 121, including hour and minute settings, are provided. Step duration selector switches 125 (see FIGS. 1 and 2) are located above each processing solution container. Similar step duration selector switches 125' on left control panel 11 provide a similar function for the paraffin containers 13, 14.

Switches 125, 125' enable selection between times 120, 121 or alternately to zero time which causes the particular step to be skipped or to unlimited time which causes the particular solution to be pumped in during automatic sequence but not pumped out. A time display 130 informs the operator of elapsed time for each solution and automatically resets when the next solution is admitted to chamber 12. A manual time display reset 131 is also provided. A hold button 137 on control panel 16 is provided and suitably connected to temporarily interrupt the timing sequence in case of emergency, et cetera.

Under an automatic mode of operation of the processor, solution pump-in, pump-out and stepping to the next solution step takes place in the appropriate preselected time sequence, throughout the designated processing solution numbers 1 through 10 and including the two paraffin steps hereinbefore described. The last paraffin step is preferably adapted to stay in chamber 12 until the operator removes the processed tissue, reseals chamber 12 and manually begins a clean out cycle by operating mode selector switch 111. Pump-out switch 115 is depressed until all of the paraffin in chamber 12 is pumped back into paraffin bath number 2. The clean out operation is started by depressing manual step button 112 which effectively moves the system up to the next solution. Pump-in button 114 is depressed and held until a desired amount of solution number 9, e.g., xylene, is pumped into chamber 12. Chamber 12 is manually cleaned with xylene solution and the excess solution is vacuum removed in the clean out operation. Next, step button 112 is depressed which moves the system up to solution number 10, e.g., absolute alcohol. Button 114 is depressed and begins pumping solution 10 into chamber 12. Button 114 is held until a desired level of solution 10 is pumped into chamber 12 and is then released stopping the pumping. Chamber 12 is further cleaned manually. Once chamber 12 is cleaned, mode selector 111 can now be set to "automatic" and chamber 12 refilled with TIMS receptacles for processing another batch of tissue specimens placed therein.

It is desirable to be able to remove the paraffin in paraffin chamber 13 since it becomes contaminated after it is used several times. Once removed, the less used paraffin in container 14 can be pumped to chamber 13 by using vacuum to draw the paraffin into chamber 12 and then pressure to force it into container 13. The paraffin in chamber 13 is drained out with the aid of manual drain 81 of chamber 13 and paraffin chamber 14 after being emptied is then charged with new paraffin.

In most processing applications, it is desirable to hold the tissue in the receptacles in the No. 1 solution (e.g., Zenker's or formalin) for several hours prior to initiating an automatic timed solution processing sequence. For such purpose, a long delay timer 134 may be employed so that the first solution may be admitted manually and the remainder of the particular program on an automatic basis after some predetermined time delay, such as in the order of four hours for short term runs or in the order of seventy-two hours for weekend runs. Suitably, an additional switch applies the delay timer 134 to that solution step.

While a wide choice of materials are available with which to construct the various components of the described apparatus it will, of course, be apparent that some of the solutions, particularly Xylene, are of a toxic and corrosive nature with respect to certain materials. The choice of material employed in constructing the processing chamber, solution containers, conduits, valves, and the like, should keep these factors in mind.

While the invention has been described primarily in terms of a light microscopy tissue processing application, it will be apparent that de-energization of the heated paraffin steps, elimination of the cleaning steps, and addition of a slide rack to the processing chamber, will render the processor highly suitable for use as an automatic mounted slide staining apparatus.

In summarizing the advantages of the present invention tissue processing method, it will be noted that a substantially closed fumeless and simplified method has been provided for fixing, dehydrating, clearing, and paraffin infusing light microscopy sized tissue in relatively large quantity. Those skilled in the art will particularly recognize the advantages of maintaining tissue in a stationary, sealed chamber during processing. In addition, the selective application of partial vacuum and pressure to the processing chamber has the two-fold effect of providing a mechanism for fluid transfer as well as a means for enhancing fluid penetration into the tissue.

The mounting of the air pump 61 and its associated piping and valves in the cabinet provides a unitary and self-contained processing apparatus with obvious advantages. However, it is recognized that the source of vacuum and pressure conditions could be obtained by use of separate external laboratory vacuum and pressure supplies fitted with electrical valves and leading direct to processing chamber 12. Also the controls could be mounted in a separate cabinet. However, this also would tend to detract from the many advantages of unifying all the necessary processing and control apparatus in a common table top mounted cabinet. Close valved coupling between the processing chamber and the one or more heated paraffin containers is most desirable to provide heated paths of minimal length to minimize the amount of heat required to keep the paraffin melted in those fluid paths which necessarily carry the paraffin back and forth to the processing chamber. The paraffin containers should preferably be immediately adjacent the processing chamber and all fluid connections for the paraffin should be of minimal length for the reasons stated. Some separation can be tolerated, however, provided any interconnecting paraffin carrying pipes are sufficiently heated and such heat is insulated as required to prevent heating those solutions which should preferably not be heated.

What is claimed is:

1. A method for processing a plurality of individual specimens of tissue to be separately contained while being simultaneously bathed for varying lengths of time in successive selected tissue solutions including melted paraffin so as to fix, dehydrate and clear the specimens preparatory to embedding, comprising:
    a. separating the specimens to be processed into groups;
    b. installing and physically isolating each group having at least one specimen per group in a respective uniform tissue receptacle which is porous to the extent of having for each of said solutions at least some portion through which the solution may be transferred;
    c. installing a plurality of such receptacles in a temperature controlled and electrically heated processing chamber having a pressure sealable top cover and then sealing the cover;

d. with the receptacles installed, the cover sealed and with the chamber positioned in proximity to a plurality of closed vented containers, each containing a particular tissue processing solution, including melted paraffin in a heated temperature controlled state, selectively and independently connecting each container to the chamber to bring the solutions including the paraffin, with the paraffin being the last solution, in a predetermined sequence to the chamber and for each such solution in the sequence:

1. establishing a vacuum condition in the chamber and
2. establishing a temperature condition in the chamber for maintaining each such predetermined volume at a selected temperature appropriate to such solution,
3. terminating the vacuum and retaining the solution for a predetermined time at a predetermined pressure and temperature, and
4. at the end of each such period of predetermined time, increasing the pressure in the chamber and thereby forcing the used solution back to its respective said container by pressure such that the selected solutions and melted paraffin are separately and independently pumped by application of vacuum and pressure to said chamber and are exchanged with each group of specimens while such specimens are confined in the chamber, held stationary and physically isolated.

2. A method as claimed in claim 1 wherein the paraffin is stored in a melted state in two separate heated, temperature-controlled containers in immediate proximity to the chamber and during each sequence melted paraffin in a first operative step is drawn from a first of such paraffin containers and in a second later operative step from the second of such containers.

3. A method as claimed in claim 2 wherein after a predetermined number of such sequences the residual paraffin in the first container is discharged to waste, the residual paraffin in the second container is pumped to the first container and the second container is refilled with a fresh supply of paraffin.

4. A method as claimed in claim 1 wherein during the sequence said chamber is subjected to an alternating pressure-vacuum cycle to effect agitation of the solution.

5. The method of claim 1 wherein all of said solutions except for the paraffin are drawn and returned through a common rotary valve placed between the chamber and solution containers and the paraffin is drawn and returned through a separately heated valved connection between the chamber and the paraffin container.

6. The method of claim 1 wherein said sequence is performed under automatic programmed control.

7. A method as claimed in claim 1 wherein the temperature in said processing chamber is controlled to be maintained at one of two temperature levels, a first lower temperature level being maintained for all solutions except paraffin, and a second higher temperature level being maintained for said paraffin.

* * * * *

UNITED STATES PATENT OFFICE
CERTIFICATE OF CORRECTION

Patent No. 4,001,460      Dated Jan. 4, 1977

Inventor(s) Thomas D. Kinney; John E. P. Pickett

It is certified that error appears in the above-identified patent and that said Letters Patent are hereby corrected as shown below:

Col. 1, line 49, the second appearance of the word "of" should be --if--.

Col. 2, line 14, --a-- should be inserted after "in".

Col. 5, line 17, "line 20" should be --chamber 12--.

Col. 5, line 19, "chamber 12" should be --line 70--.

Col. 8, line 39, "indicated" should be --indicate--.

Col. 11, lines 14 and 15, "establishing a vacuum condition in the chamber and" should be deleted and --drawing the respective solution into the chamber in a predetermined volume by establishing a vacuum condition in the chamber-- should be inserted.

Signed and Sealed this

Fifth Day of April 1977

[SEAL]

Attest:

RUTH C. MASON
Attesting Officer

C. MARSHALL DANN
Commissioner of Patents and Trademarks